United States Patent
Iida et al.

(10) Patent No.: US 10,863,883 B2
(45) Date of Patent: Dec. 15, 2020

(54) MEDICAL SYSTEM AND TREATMENT TOOL CALIBRATING METHOD

(71) Applicant: OLYMPUS CORPORATION, Tokyo (JP)

(72) Inventors: Masatoshi Iida, Tokyo (JP); Naoya Hatakeyama, Tokyo (JP); Hiroshi Wakai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 523 days.

(21) Appl. No.: 15/245,269

(22) Filed: Aug. 24, 2016

(65) Prior Publication Data

US 2016/0360947 A1 Dec. 15, 2016

Related U.S. Application Data

(63) Continuation of application No. PCT/JP2015/055599, filed on Feb. 26, 2015.

(30) Foreign Application Priority Data

Feb. 27, 2014 (JP) ................................. 2014-036824

(51) Int. Cl.
 *A61B 1/00* (2006.01)
 *B25J 9/16* (2006.01)
 (Continued)

(52) U.S. Cl.
 CPC ...... *A61B 1/00006* (2013.01); *A61B 1/00009* (2013.01); *A61B 1/00045* (2013.01);
 (Continued)

(58) Field of Classification Search
 CPC ... A61B 34/30; A61B 2034/301; A61B 34/37; A61B 2034/2061; A61B 1/00057;
 (Continued)

(56) References Cited

U.S. PATENT DOCUMENTS

| 2004/0138530 | A1 | 7/2004 | Kawai et al. |
| 2008/0004603 | A1* | 1/2008 | Larkin ............... B25J 9/1692 606/1 |

(Continued)

FOREIGN PATENT DOCUMENTS

| CN | 101422901 A | 5/2009 |
| CN | 101444415 A | 6/2009 |

(Continued)

OTHER PUBLICATIONS

International Search Report dated May 19, 2105 issued in PCT/JP2015/055599.

(Continued)

*Primary Examiner* — Alexandra L Newton

(74) *Attorney, Agent, or Firm* — Scully, Scott, Murphy & Presser, P.C.

(57) ABSTRACT

A medical system includes a treatment tool including a treatment portion, a joint portion, a flexible tube portion, and a drive unit; an endoscope device including an outer sheath that holds the treatment tool and an imaging unit that is capable of acquiring an image including at least the joint portion; and a control unit that controls an operation of the treatment tool. The control unit includes a table that has a parameter for causing the joint portion to move, a controller that issues a command for controlling the drive unit based on the parameter to the drive unit, an image processing unit that calculates at least one of a position and an orientation of the joint portion based on the image, and a compensation value calculating unit that detects displacement of the joint portion, generates a compensation value, and incorporates the compensation value into the parameter.

8 Claims, 11 Drawing Sheets

(51) Int. Cl.
  *G02B 23/24*    (2006.01)
  *A61B 34/30*    (2016.01)
  *A61B 1/04*     (2006.01)
  *A61B 34/20*    (2016.01)
  *A61B 34/37*    (2016.01)
  *A61B 1/005*    (2006.01)
  *A61B 1/05*     (2006.01)
  *A61B 17/00*    (2006.01)
  *A61B 90/00*    (2016.01)

(52) U.S. Cl.
  CPC ........ *A61B 1/0051* (2013.01); *A61B 1/00057* (2013.01); *A61B 1/00059* (2013.01); *A61B 1/00087* (2013.01); *A61B 1/04* (2013.01); *A61B 1/05* (2013.01); *A61B 34/20* (2016.02); *A61B 34/30* (2016.02); *A61B 34/37* (2016.02); *B25J 9/1692* (2013.01); *G02B 23/2476* (2013.01); *A61B 2017/00725* (2013.01); *A61B 2034/2065* (2016.02); *A61B 2034/301* (2016.02); *A61B 2090/364* (2016.02)

(58) Field of Classification Search
  CPC ............... A61B 1/00149; A61B 34/20; A61B 2017/00725; A61B 1/00147
  USPC .......................................... 600/114, 117, 118
  See application file for complete search history.

(56) References Cited

U.S. PATENT DOCUMENTS

| | | | |
|---|---|---|---|
| 2008/0103491 A1 | 5/2008 | Omori et al. | |
| 2008/0114494 A1 | 5/2008 | Nixon | |
| 2009/0012365 A1 | 1/2009 | Ueno et al. | |
| 2009/0112060 A1 | 4/2009 | Sugiyama et al. | |
| 2009/0112316 A1 | 4/2009 | Umemoto et al. | |
| 2010/0030023 A1* | 2/2010 | Yoshie | A61B 1/00147 600/117 |
| 2010/0082041 A1 | 4/2010 | Prisco | |
| 2010/0169815 A1* | 7/2010 | Zhao | B25J 9/1633 715/771 |
| 2013/0345517 A1* | 12/2013 | Morimoto | H05B 47/10 600/178 |

FOREIGN PATENT DOCUMENTS

| | | |
|---|---|---|
| GB | 2 448 421 A | 10/2008 |
| JP | S58-0217015 A | 12/1983 |
| JP | H05-80842 A | 4/1993 |
| JP | H10-174686 A | 6/1998 |
| JP | 2004-041538 A | 2/2004 |
| JP | 2007-029167 A | 2/2007 |
| JP | 2007-260298 A | 10/2007 |
| JP | 2008-104854 A | 5/2008 |
| JP | 2009-101077 A | 5/2009 |
| JP | 2009-107074 A | 5/2009 |
| JP | 2010-214128 A | 9/2010 |
| JP | 2012-504016 A | 2/2012 |
| WO | 2012/153646 A1 | 11/2012 |

OTHER PUBLICATIONS

Extended Supplementary European Search Report dated Oct. 27, 2017 in European Patent Application No. 15 75 4565.8.
Japanese Office Action dated Jun. 6, 2017 in Japanese Patent Application No. 2014-036824.
Chinese Office Action dated Jun. 26, 2017 in Chinese Patent Application No. 201580007642.7.
Notice of Allowance dated Dec. 5, 2017 in Japanese Patent Application No. 2014-036824.

* cited by examiner

MEDICAL SYSTEM AND TREATMENT TOOL CALIBRATING METHOD

This application is a continuation application based on a PCT International Application No. PCT/JP2015/055599, filed on Feb. 26, 2015, whose priority is claimed on Japanese Patent Application No. 2014-036824, filed on Feb. 27, 2014. The contents of both the PCT International Application and the Japanese Patent Application are incorporated herein by reference.

BACKGROUND OF THE INVENTION

Field of the Invention

The present invention relates to a medical system and a treatment tool calibrating method.

Description of Related Art

A medical system that drives a treatment tool of a manipulator using a rotational force of a motor via a wire is known. In the medical system, calibration is performed by moving one of a pair of gripping members of the manipulator to the other gripping member and measuring the displacement position and the torque value of the gripping member.

In the case of a flexible manipulator, since the manipulator is curved in the process of guiding the manipulator to a treatment target part, a path of the wire in the manipulator is changed. In the technique described in United States Patent Application, Publication No. 2008/0114494, it is difficult to perform calibration in consideration of the influence of the change of the path of the wire in the manipulator.

SUMMARY OF THE INVENTION

A medical system according to an aspect of the present invention includes: a treatment tool including a treatment portion that performs treatment on a living body; a joint portion that moves the treatment portion; a flexible tube portion that is connected to the joint portion; and a drive unit that is connected to the flexible tube portion and displaces the joint portion; an endoscope device including a flexible outer sheath that has a distal end and a proximal end, the outer sheath being provided to hold the treatment tool such that the treatment portion protrudes from the distal end, and an imaging unit that is capable of acquiring at least an image including at least the joint portion in an imaging field of view; and a control unit that controls an operation of the treatment tool based on the image; wherein the control unit includes a table that has a parameter for causing the joint portion to move, a controller that issues a command for controlling the drive unit based on the parameter to the drive unit, an image processing unit that calculates at least one of a position and an orientation of the joint portion based on the image, and a compensation value calculating unit that detects displacement of the joint portion, generates a compensation value, and incorporates the compensation value into the parameter, the displacement of the joint portion being detected based on at least one of the position and the orientation of the joint portion calculated by the image processing unit, and the compensation value being generated for compensating for a difference between the command and the displacement of the joint portion.

DETAILED DESCRIPTION OF THE INVENTION

Figure 1:
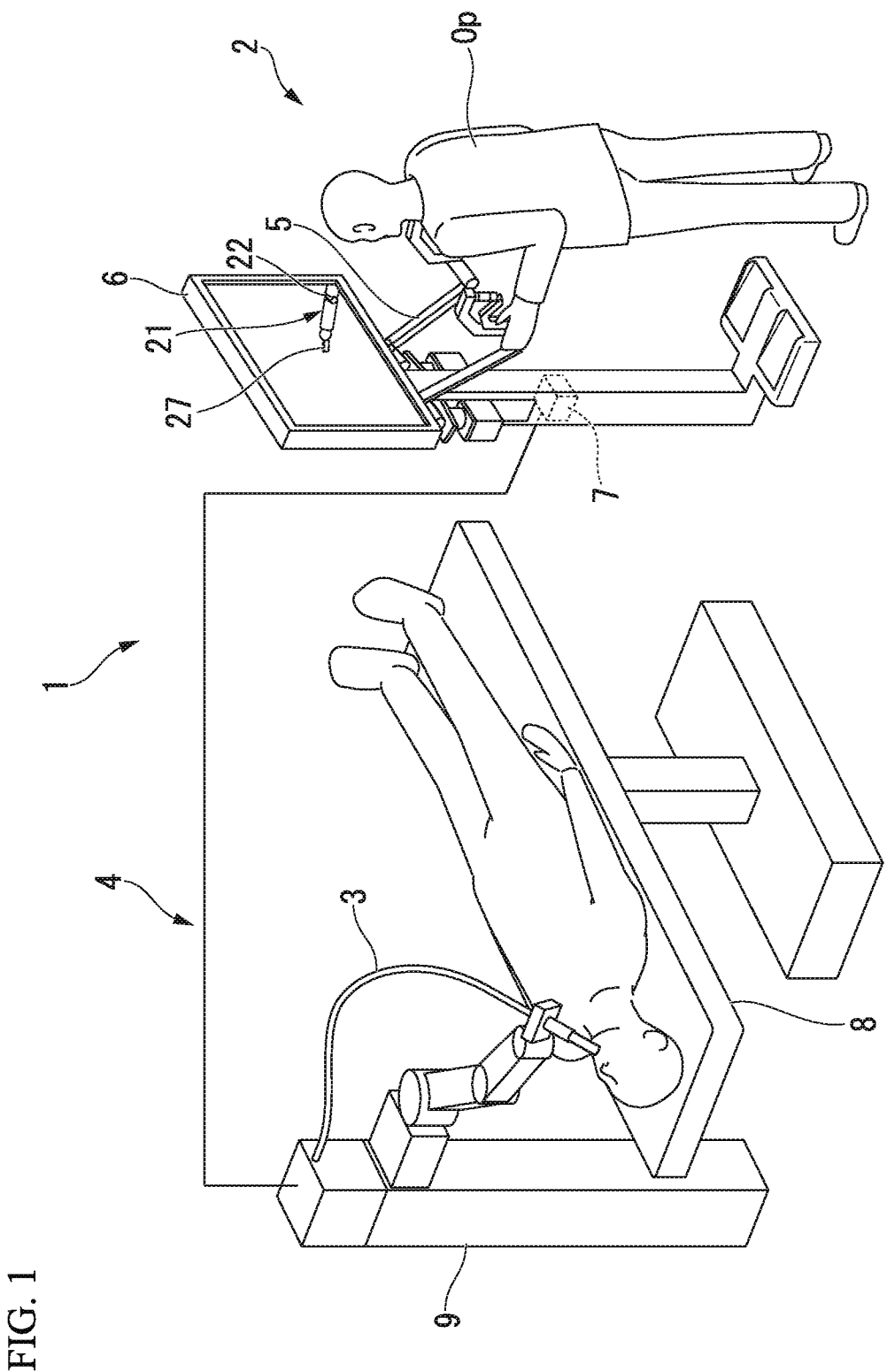
FIG. 1 is a perspective view schematically showing an entire configuration of a medical system according to a first embodiment.

Hereinafter, a medical system according to embodiments will be described with reference to the accompanying drawings. In the drawings, scales of members are appropriately changed to make the members recognizable.

First Embodiment

FIG. 1 is a perspective view schematically showing an entire configuration of a medical system according to a first embodiment. The medical system according to this embodiment is a so-called master-slave system. That is, as shown in FIG. 1, the medical system 1 includes a master manipulator 2 that is manipulated by an operator Op for treatment, a slave manipulator 4 that is provided with an endoscope device 3, and a control unit 50 (see FIG. 4) that controls the slave manipulator 4 in response to the manipulation of the master manipulator 2.

The master manipulator 2 includes a master arm 5 that is manipulated by an operator Op, a display device 6 that displays image information (see FIG. 4) 59 such as an image captured using the endoscope device 3, and a controller 7 of a control unit 50 to be described later.

The master arm 5 is a manipulation unit that is disposed to actuate the endoscope device 3. Although details are not shown, two master arms 5 disposed in the master manipulator 2 are provided to correspond to a right hand and a left hand of an operator Op. The master arm 5 has a multi-joint structure configured to cause a joint portion 22 of a treatment tool 21, which is a mechanism disposed in the body with at least one degree of freedom, to operate.

The display device 6 is a device on which an image of a treatment target part which is captured by an observation device (see FIG. 2) attached to the endoscope device 3 is displayed. The joint portion 22 of the treatment tool 21 along with the treatment target part is displayed on the display device 6.

The controller 7 generates a manipulation command for causing the slave manipulator 4 to operate based on the operation of the master arm 5.

The slave manipulator 4 includes a surgical table 8 on which a patient is placed, a multi-joint robot 9 that is disposed around the surgical table 8, and an endoscope device 3 that is attached to the multi-joint robot 9. The multi-joint robot 9 operates in accordance with a manipulation command issued from the master manipulator 2.

Figure 2:
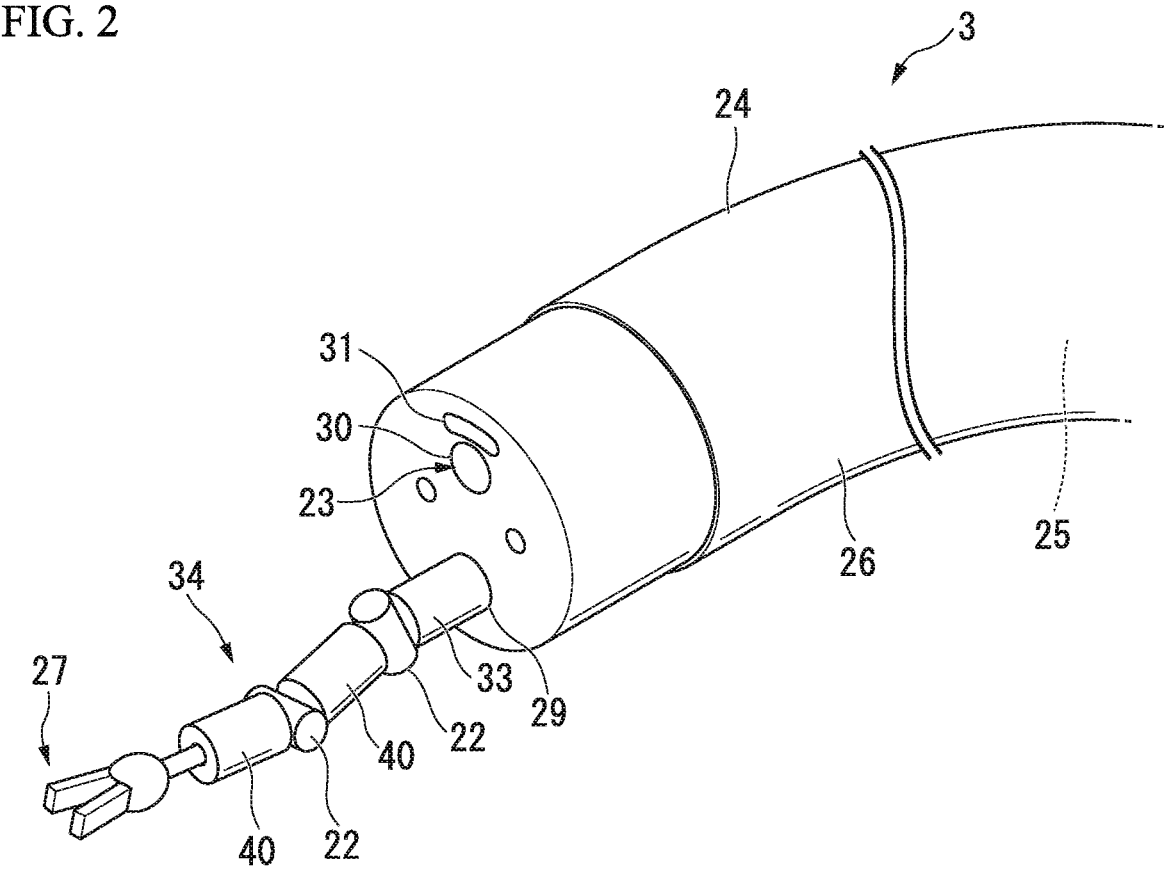
FIG. 2 is a perspective view of an endoscope device in the medical system according to the first embodiment.

FIG. 2 is a perspective view of the endoscope device in the medical system according to the first embodiment. As shown in FIG. 2, the endoscope device 3 includes an insertion portion 24 and an outer sheath driving unit (drive unit) 25.

The insertion portion 24 includes an outer sheath 26 and an observation device 23.

The outer sheath 26 is a flexible long member that is inserted into the body of a patient. The outer sheath 26 has a distal end and a proximal end and also includes a treatment tool channel 29 into which the treatment tool 21 can be inserted.

The observation device 23 is a device in which an imaging field of view directed to the distal end side from the distal end of the outer sheath 26 is set and can acquire and output an image of a treatment target part and the treatment tool 21 to the display device 6. In this embodiment, the observation device 23 is disposed in a distal end portion of the outer sheath 26. The observation device 23 includes an imaging unit 30 and an illumination unit 31.

The imaging unit 30 can acquire at least one image including at least the joint portion 22 in the imaging field of view.

The illumination unit 30 emits illumination light to the imaging field of view of the imaging unit 30.

The observation device 23 may be detachable from the outer sheath 26. For example, a known endoscope device may be used as the observation device and an endoscope channel into which the known endoscope device can be inserted may be formed in the outer sheath 26.

The treatment tool channel 29 holds the treatment tool 21 such that the treatment portion 27 of the treatment tool 21 protrudes from the distal end of the insertion portion 24.

The outer sheath driving unit 25 is disposed on the proximal end side of the outer sheath 26, and can cause the observation device 23 and the treatment portion 27 of the treatment tool 21 in the body to face a desired direction by curving the distal end portion of the outer sheath 26 by driving.

Figure 3:
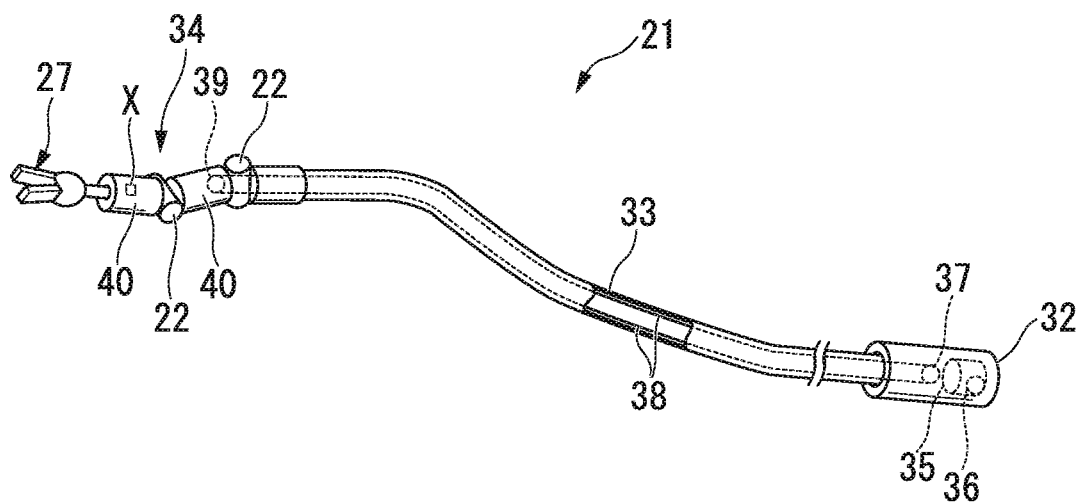
FIG. 3 is a partially exploded perspective view of a treatment tool in the medical system according to the first embodiment.

FIG. 3 is a partially exploded perspective view of the treatment tool in the medical system according to the first embodiment. As shown in FIG. 3, the treatment tool 21 includes a treatment tool driving unit (drive unit) 32, a flexible portion 33 which is a flexible tube portion, and a distal portion 34.

The treatment tool driving unit 32 includes a motor 35, an encoder 36, a driving-side rotary body 37, a wire 38, and a driven-side rotary body 39.

The motor 35 is disposed for each degree of freedom of the joint portion 22 and the treatment portion 27. In this embodiment, only one motor 35 for curving one joint portion 22 will be described. The treatment tool driving unit 32 can independently drive another joint portion 22 which is not shown and another treatment portion 27 which is not shown using another motor which is not shown.

A motor shaft of the motor 35 is connected to the driving-side rotary body 37 via a reduction gear which is not shown. A stepping motor or the like may be employed as the motor 35.

The encoder 36 (see FIG. 4) is attached to the motor shaft, which is not shown, of the motor 35 in a non-contact manner. The encoder 36 is electrically connected to the control unit 50.

An example of the driving-side rotary body 37 is a pulley that rotates with a driving force which the motor 35 generates. One end of the wire 38 is suspended on the driving-side rotary body 37.

The wire 38 is an annular wire of which one end is suspended on the driving-side rotary body 37, an intermediate portion is movably accommodated in the flexible portion 33, and the other end is suspended on the driven-side rotary body 39.

The flexible portion 33 has a flexible tubular shape. The treatment tool driving unit 32 is disposed at the proximal end of the flexible portion 33, and the treatment portion 27 is disposed at the distal end of the flexible portion 33.

The distal portion 34 of the treatment tool 21 includes a joint portion 22, an arm portion 40, and a treatment portion 27.

The joint portion 22 is coupled to the arm portion 40. The joint portion 22 displaces the arm portion 40 by transmission of an amount of force from the driven-side rotary body 39. A structure with which the joint portion 22 is curved is not limited to the joint structure. For example, a joint structure in which a plurality of curving pieces are rotatably coupled may be employed.

The treatment portion 27 is a forceps or an incision knife for performing treatment on a treatment target.

In this embodiment, the distal portion 34 of the treatment tool 21 has an identification portion X for identifying the type of the treatment tool 21. The identification portion X is disposed in the arm portion 40, for example, by printing or carving In the treatment tool 21, the driving-side rotary body 37 rotates with the rotation of the motor 35 and the driven-side rotary body 39 rotates via the wire 38. Accordingly, the joint portion 22 is curved by the rotation of the driven-side rotary body 39. At this time, a rotation signal from the encoder 36 is processed by the control unit 50 and is received as information of a degree of motor drive.

Figure 4:
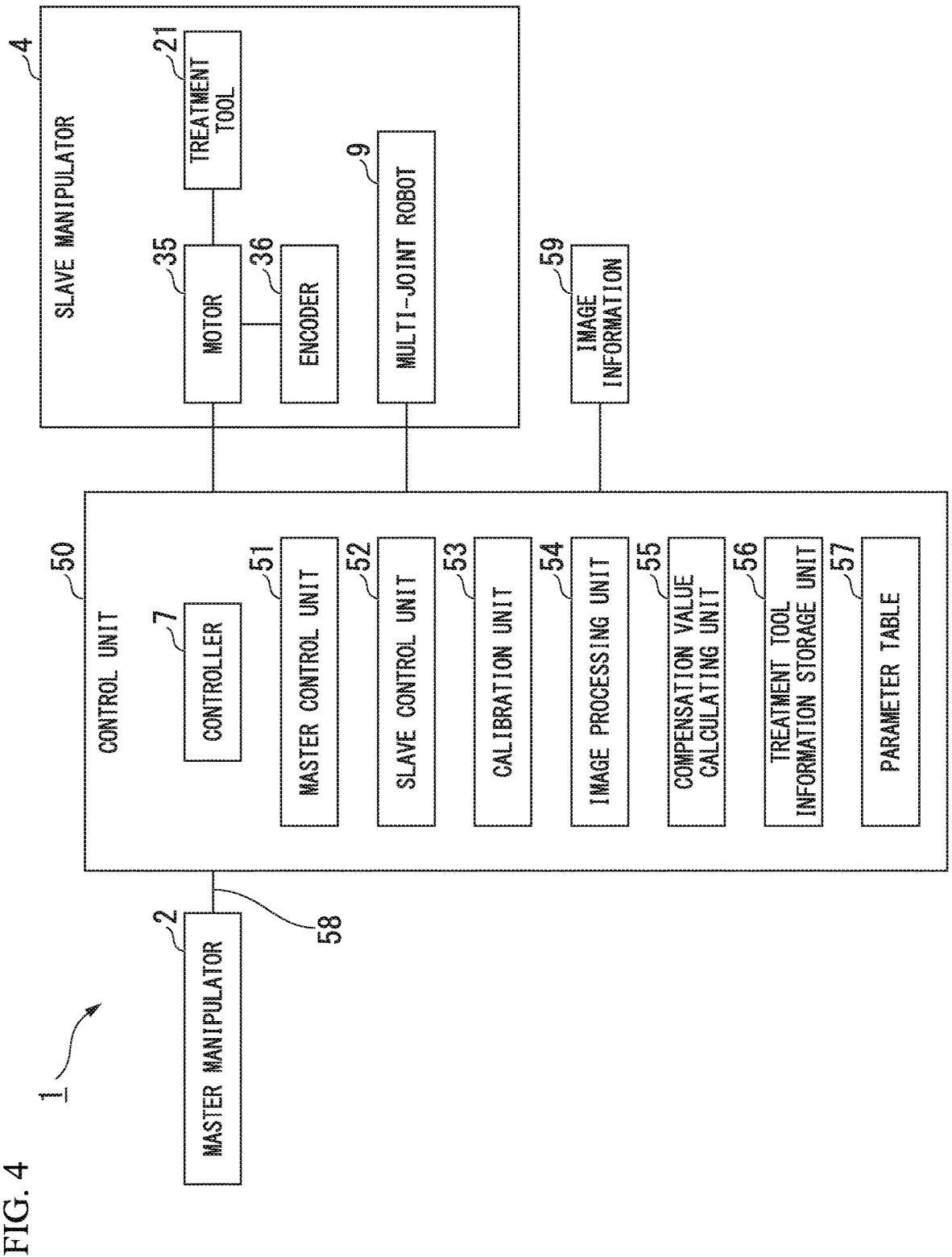
FIG. 4 is a block diagram showing an example of the medical system according to the first embodiment.

FIG. 4 is a block diagram showing an example of the medical system according to the first embodiment. This block diagram will also be used in subsequent embodiments.

As shown in FIG. 4, the control unit 50 of the medical system 1 includes a master control unit 51, a slave control unit 52, a calibration unit 53, an image processing unit 54, a compensation value calculating unit 55, a treatment tool information storage unit 56, a parameter table 57, and a controller 7.

The master control unit 51 receives and processes a manipulation input (input) 58 in the master manipulator 2.

The slave control unit 52 outputs drive signals for the multi-joint robot 9, the endoscope device 3, and the treatment tool 21 based on a command from the master control unit 51.

The calibration unit 53 generates a parameter for compensating for an operation of the treatment tool 21. The calibration unit 53 may be included in any one of the master control unit 51 and the slave control unit 52 or may be independent from the master control unit 51 and the slave control unit 52.

The image processing unit 54 analyzes the image information 59 acquired by the imaging unit 30. Here, the image processing unit 54 calculates at least one of a position and an orientation of the joint portion 22 based on the image information 59. The image processing unit 54 in this embodiment calculates a joint angle of the joint portion 22 through image recognition using the image information 59.

The compensation value calculating unit 55 detects displacement of the joint portion 22 based on at least one of the position and the orientation of the joint portion 22 which is calculated by the image processing unit 54, generates a compensation value for compensating for a difference between the input (command) 58 and the displacement of the joint portion 22, and incorporates the compensation value into the parameter. Specifically, the compensation value calculating unit 55 according to this embodiment incorporates a hysteresis width to be described later as the compensation value into the parameter. The compensation value calculating unit 55 calculates the hysteresis width based on an amount of drive of the treatment tool driving unit 32 until displacement of the joint portion 22 is started after the command is issued, and determines and incorporates the compensation value after displacement of the joint portion 22 is started.

The treatment tool information storage unit 56 stores individual data required for calibration such as individual information of the treatment tool 21 or a pattern matching image.

The parameter table 57 includes parameters which are referred to by the controller 7. An initial parameter is loaded into the parameter table 57 when the medical system 1 is started. The initial parameter loaded into the parameter table 57 is updated with every calibration by the compensation value calculating unit 55 and becomes a parameter which is referred to by the controller 7.

The controller 7 issues an output to the motor 35 using the parameter which is updated by the calibration unit 53 and stored in the parameter table 57.

The control unit 50 performs calibration through the use of the calibration unit 53 using the image information 59 which is acquired by the imaging unit 30. Here, when the treatment tool 21 does not appear in the imaging field of view of the imaging unit 30, the control unit 50 controls the position of the treatment tool 21 such that the treatment tool 21 moves to a position at which calibration can be suitably performed on the treatment tool 21. For example, when the joint portion 22 cannot be specified in the image information 59, the control unit 50 displaces the joint portion 22 until the joint portion 22 appears in the image information 59.

In another control method, when the joint portion 22 cannot be specified in the image information 59, the control unit 50 may determine that the joint portion 22 is located outside the imaging field of view of the imaging unit 30 and may output instruction image information in which a specifiable area for the joint portion 22 is superimposed on the image information 59 to the display device 6 instead of the image information 59. That is, in this control method, the control unit 50 supports a user's manipulation such that the treatment tool 21 enters a calibratable range by encouraging the user of the medical system 1 to move the treatment tool 21. When the instruction image information is received instead of the image information 59, the instruction image information is displayed on the display device 6. After the joint portion 22 of the treatment tool 21 is disposed in the specifiable area in the imaging field of view of the imaging unit 30, the image processing unit 54 calculates at least one of the position and the orientation of the joint portion 22 using the image information 59 in which the joint portion 22 is located in the specifiable area.

Figure 5:
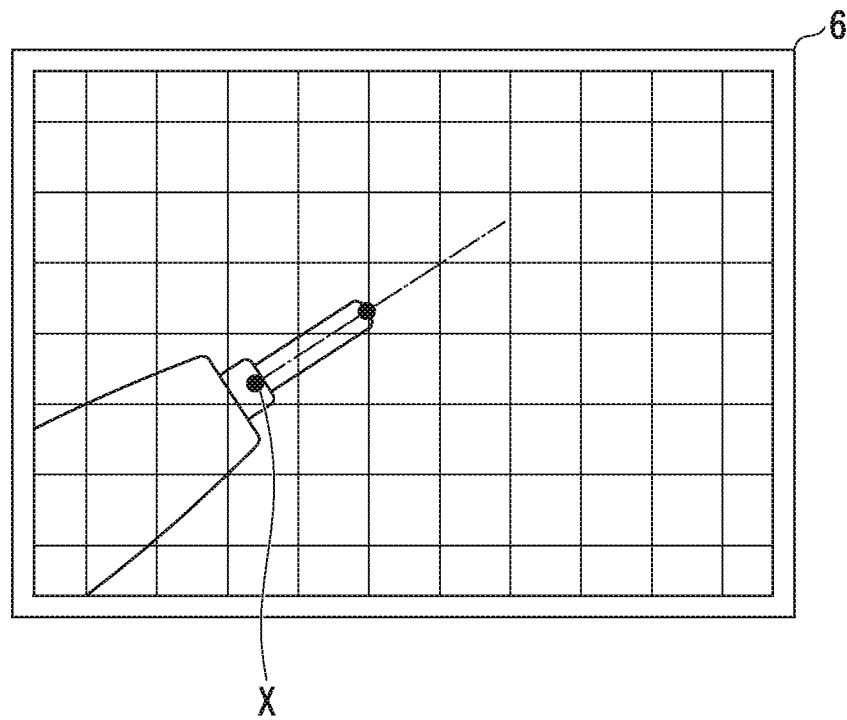
FIG. 5 is a diagram showing an example of an image of a display device in the medical system according to the first embodiment.

FIG. 5 is a diagram showing an example of an image on the display device in the medical system according to the first embodiment. As shown in FIG. 5, the calibration unit 53 performs calibration based on the image information 59 displayed on the display device 6. For example, the control unit 50 sets a bent point of the joint portion 22 as a virtual feature point by image recognition from the image information 59 and calculates the bending angle of the joint portion 22.

Figure 6:
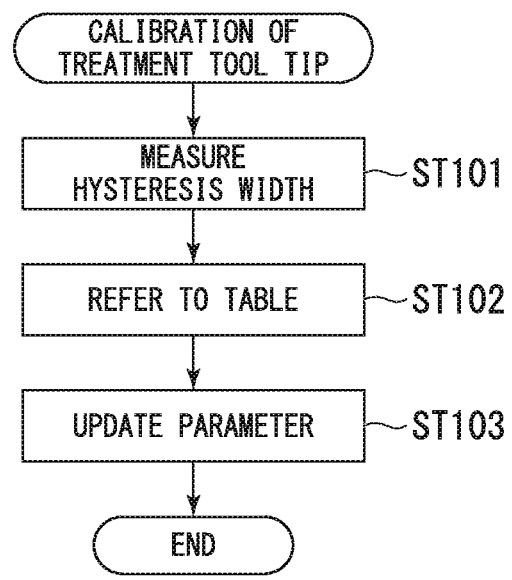
FIG. 6 is a flowchart showing calibration in the medical system according to the first embodiment.

FIG. 6 is a flowchart showing calibration in the medical system according to the first embodiment. As shown in FIG. 6, in calibration of a treatment tool tip, first, a hysteresis width $\Delta\theta$ is measured (MEASUREMENT OF HYSTERESIS WIDTH, step ST101). Here, the measurement of the hysteresis width $\Delta\theta$ is a value based on an amount of drive of the treatment tool driving unit 32 until displacement of the joint portion 22 is started after a command is issued.

Then, with reference to the parameter stored in the parameter table 57 (REFER TO TABLE (step ST102)), a hysteresis value is updated (UPDATE PARAMETER, step ST103). Here, the hysteresis value is defined as a parameter element having a function including the hysteresis width $\Delta x$ as a variable. For example, the hysteresis value is expressed by Equation (1).

$$u = \Delta\theta \cdot sgn(\dot{\theta}_{ref}) \quad \text{Equation (1)}$$

Here, $\dot{\theta}_{ref}$ is a first differential of $\theta_{ref}$.

The symbol u in Equation (1) denotes the hysteresis value and is the compensation value in this embodiment. The hysteresis value is stored in the parameter table 57 and is read as an updated parameter when the controller 7 is activated. The symbol sgn denotes a sign function that has +1, 0, or −1 depending on plus, 0, or minus of an argument.

Then, the calibration is performed using the updated hysteresis value. The hysteresis width is acquired through the flowchart shown in FIG. 7.

Figure 7:
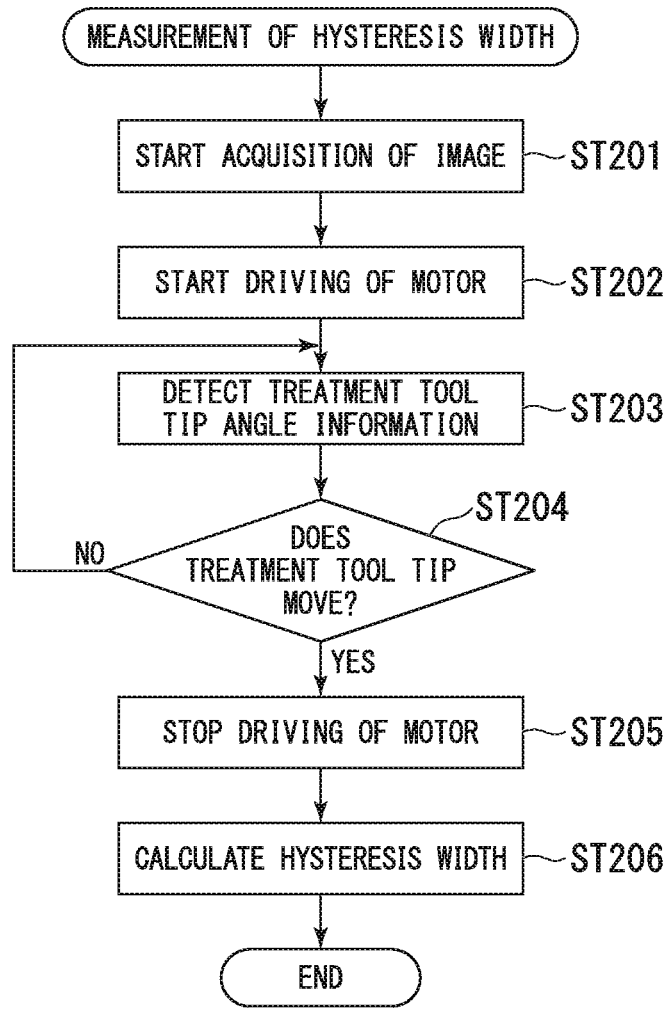
FIG. 7 is a flowchart showing an example in which a hysteresis width in the medical system according to the first embodiment is measured.

FIG. 7 is a flowchart showing an example in which the hysteresis width in the medical system according to the first embodiment is measured.

As shown in FIG. 7, in measuring the hysteresis width, at least one image including at least the joint portion 22 in the imaging field of view is acquired by the imaging unit 30 (START ACQUISITION OF IMAGE, step ST201). For example, the image acquired by the imaging unit 30 is displayed on the display device 6 in a state in which the joint portion 22 is included in the image.

In a state in which imaging is performed by the imaging unit 30, driving of the motor 35 of the treatment tool driving unit 32 is started (START DRIVING OF MOTOR, step ST202). Movement of the joint portion 22 is started with the driving of the motor 35. However, a delay or other difference may occur between the driving of the motor 35 and the bending of the joint portion 22 due to elongation or looseness of the wire 38, a frictional force against the outer surface of the wire 38, or the like. For example, even when the motor 35 is driven, the joint portion 22 may not operate at all until the motor 35 reaches a predetermined rotational angle.

From the time point at which the driving of the motor 35 is started, detection of the treatment tool tip angle information is started (DETECT TREATMENT TOOL TIP ANGLE INFORMATION, step ST203). That is, movement of the moving joint portion 22 is detected. The treatment tool tip angle information can be detected by pattern matching or an optical flow to be described later.

Here, it is detected whether the joint portion 22 moves (DOES TREATMENT TOOL TIP MOVE?, step ST204).

At this time, when the joint portion 22 does not move, the treatment tool tip angle information is repeatedly detected (DETECT TREATMENT TOOL TIP ANGLE INFORMATION, step ST203).

On the other hand, when the joint portion 22 moves, the driving of the motor 35 is temporarily stopped (STOP DRIVING OF MOTOR, step ST205).

When the initial value of the distal portion 34 is known, the hysteresis width can be calculated by moving the distal portion 34 in one direction. When the initial value of the distal portion 34 is not known, the hysteresis width can be calculated with the initial value unknown by causing the distal portion 34 to reciprocate in two opposite directions (for example, right and left directions). For example, the motor 35 is driven to move the distal portion 34 in a predetermined direction, the degree of drive of the motor 35 when minute movement of the distal portion 34 is detected is stored, the motor 35 is driven to move the distal portion in the opposite direction of the predetermined direction, and the degree of drive of the motor 35 when minute movement of the distal portion 34 is detected is stored. The hysteresis width can be calculated from two pieces of drive information acquired in this process.

Until displacement of the joint portion 22 is started after a command is issued, the hysteresis width based on the degree of drive of the treatment tool driving unit 32 is calculated to determine the hysteresis value and is set as the compensation value u by the compensation value calculating unit 55 (CALCULATE HYSTERESIS WIDTH, step ST206). In this way, the motor 35 is driven until the joint portion 22 moves minutely, and the hysteresis width is calculated based on the degree of drive of the treatment tool driving unit 32.

Figure 8:
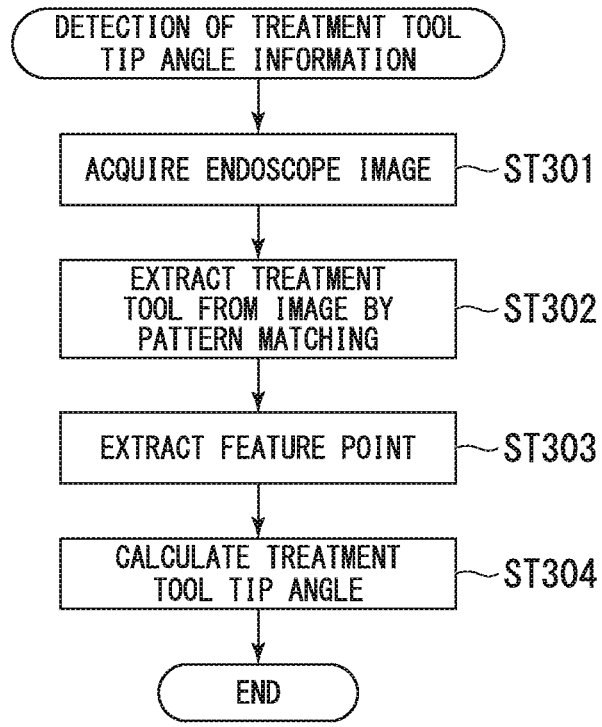
FIG. 8 is a flowchart showing an example in which tip angle information of the treatment tool in the medical system according to the first embodiment is detected.

FIG. 8 is a flowchart showing an example in which the treatment tool tip angle information in the medical system according to the first embodiment is detected.

As shown in FIG. 8, first, image information 59 is acquired by the imaging unit 30 of the endoscope device 3 (ACQUIRE ENDOSCOPE IMAGE, step ST301).

Then, image information 59 of the treatment tool 21 is extracted from the acquired image information 59 by pattern matching with reference to a predetermined pattern based on the identification portion X (EXTRACT TREATMENT TOOL FROM IMAGE BY PATTERN MATCHING step ST302).

Subsequently, a feature point is extracted from the extracted image information 59 (EXTRACT FEATURE POINT, step ST303).

Then, angle information of the distal portion 34 of the treatment tool 21 is calculated from the extracted feature point (CALCULATE TREATMENT TOOL TIP ANGLE, step ST304).

Figure 9:
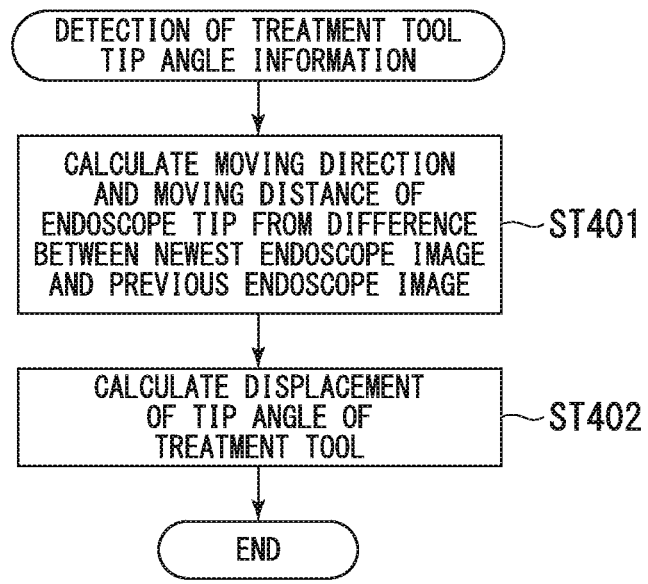
FIG. 9 is a flowchart showing another example in which the tip angle information of the treatment tool in the medical system according to the first embodiment is detected.

FIG. 9 is a flowchart showing another example in which the treatment tool tip angle information in the medical system according to the first embodiment is detected. As shown in FIG. 9, the image information 59 acquired by the endoscope device 3 is processed in an optical flow manner. That is, the image processing unit 54 calculates displacement of the joint portion 22 from a difference between newest image information 59 and image information 59 acquired immediately before the newest image information 59 is acquired in time series in the image information 59. That is, first, the newest image information 59 of the endoscope device 3 is acquired. Then, the previous image information 59 of the endoscope device 3 is acquired and a difference between both pieces of image information 59 is calculated, whereby a moving direction and a moving distance of the endoscope tip are calculated (CALCULATE MOVING DIRECTION AND MOVING DISTANCE OF ENDOSCOPE TIP FROM DIFFERENCE BETWEEN NEWEST ENDOSCOPE IMAGE AND PREVIOUS ENDOSCOPE IMAGE, step ST401).

Then, displacement of the angle of the distal portion 34 of the treatment tool 21 is calculated (CALCULATE DISPLACEMENT OF TIP ANGLE OF TREATMENT TOOL, step ST402).

According to the above-mentioned first embodiment, since the control unit 50 includes the parameter table 57, the controller 7, the image processing unit 54, and the compensation value calculating unit 55, calibration is performed in consideration of a variation in operation of the distal portion 34 of the treatment tool 21 due to a variation in characteristics of the wire 38. Accordingly, it is possible to perform appropriate calibration when the distal portion 34 of the treatment tool 21 is guided to a treatment target part in the endoscope device 3 according to this embodiment.

According to the first embodiment, since the bending angle of the joint portion 22 of the treatment tool 21 can be calculated using the pattern matching or the optical flow by the image processing unit 54, the imaging unit 30 essential for observing a treatment target part can be used as an element for calibration. Accordingly, an encoder that detects the joint angle of the joint portion 22 is not necessary and it is possible to perform high-accuracy calibration with a simple configuration.

According to the first embodiment, when the joint portion 22 cannot be specified in the image information 59, the control unit 50 displaces the joint portion 22 until the joint portion 22 appears in the image information 59. Accordingly, it is possible to avoid a situation in which calibration is not possible.

When an instruction image in which the specifiable area for the joint portion 22 is superimposed on the image information 59 is output to the display device 6 instead of the image information 59 to encourage a user to move the treatment tool 21, the manipulation of the treatment tool 21 is put in the hands of the user of the treatment tool 21 and it is thus possible to move the treatment tool 21 stably. The calibration may be automatically started when the treatment tool 21 is moved to an appropriate position by the user. In this case, it is possible to simplify a manipulation to be performed by the user.

According to the first embodiment, since the control unit 50 specifies the treatment tool 21 based on the identification portion X, it is possible to detect the treatment tool 21 by simple image processing.

In the above-mentioned embodiment, one of the pattern matching and the optical flow is employed, but a configuration in which an image can be processed using both the pattern matching and the optical flow may be employed. For example, the pattern matching may be employed when the identification portion X is specifiable and a pattern matching image is present, and the optical flow may be employed when the identification portion X is not specifiable or an appropriate pattern matching image is not present. That is, a configuration capable of selecting one of the pattern matching and the optical flow depending on a situation may be employed.

According to the first embodiment, since the compensation value calculating unit 55 calculates the hysteresis width based on the degree of drive of the treatment tool driving unit 32 until the displacement of the joint portion 22 is started after a command is issued and sets the compensation value, it is possible to acquire an appropriate compensation value using the measured value of the distal portion 34 of the treatment tool 21.

According to the first embodiment, since the control unit 50 changes the parameter to correspond to the treatment tool 21 specified based on the identification portion X, it is possible to accurately detect the treatment tool 21.

Second Embodiment

A second embodiment of the present invention will be described below.

Figure 10:
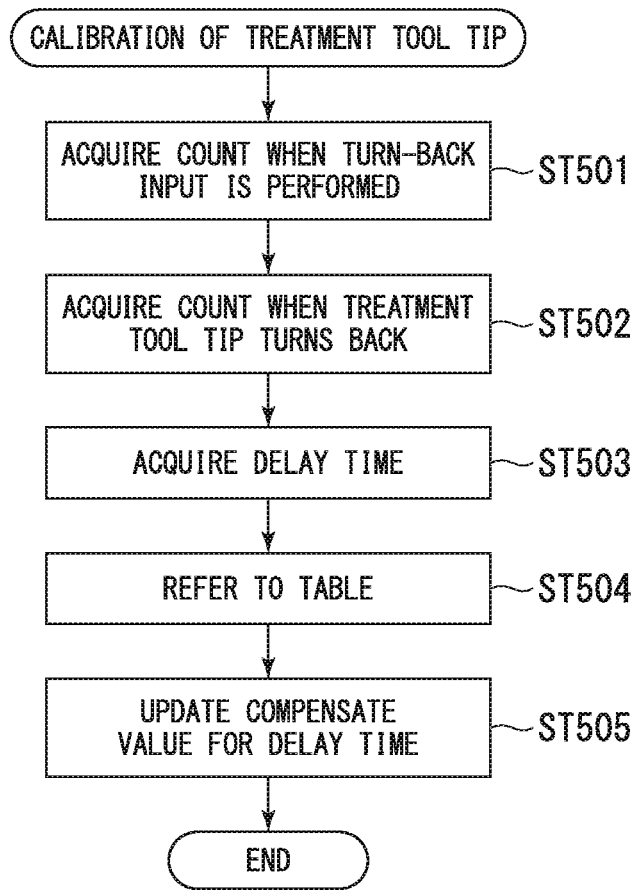
FIG. 10 is a flowchart showing calibration in a medical system according to a second embodiment.

FIG. 10 is a flowchart showing calibration in a medical system according to the second embodiment. In the following embodiments, the same elements as in the first embodiment will be referenced by the same reference signs, a description thereof will not be repeated, and only differences will be described.

As shown in FIG. 10, this embodiment is different from the above-mentioned embodiment in the calibration order in the control unit 50. In the calibration according to this embodiment, a delay time until the distal portion 34 of the treatment tool 21 starts its turn-back in accordance with a command for turning back the distal portion 34 of the treatment tool 21 after the command is issued is used. In this embodiment, "turn-back" refers to switching of a displacement direction such that the distal portion 34 is displaced in the opposite direction in a state in which the distal portion 34 is displaced in a predetermined direction.

In the calibration according to this embodiment, first, a count value when a turn-back command is issued is acquired (ACQUIRE COUNT WHEN TURN-BACK INPUT IS PERFORMED, step ST501). In the acquisition of the count value, a time point at which the turn-back command is issued is set to zero, for example, by resetting a timer which is not shown to zero and starting count-up.

Then, a count value when the distal portion 34 of the treatment tool 21 starts the turn-back in accordance with the turn-back command is acquired (ACQUIRE COUNT WHEN TREATMENT TOOL TIP TURNS BACK, step ST502). It can be detected that the distal portion 34 of the treatment tool 21 starts the turn-back by detecting displacement of the distal portion 34 using the pattern matching or the optical flow which is described in the first embodiment.

Subsequently, a delay time until the distal portion 34 of the treatment tool 21 starts the turn-back after the turn-back command is issued is acquired (ACQUIRE DELAY TIME, step ST503). In this embodiment, the count value of the timer which is reset to zero when the turn-back command is issued is acquired as the delay time.

Then, the parameter table 57 is referred to (REFER TO TABLE, step ST504) and then the compensation value of the delay time is updated (UPDATE COMPENSATE VALUE FOR DELAY TIME, step ST505). Here, the delay time can be compensated for by a phase advance filter expressed by Equation (2) and control compensation expressed by Equation (3). In Equation (2), the symbol ΔT denotes a time constant and the symbol s denotes a Laplacian operator. The phase advance filter may be set from the time constant.

$$\frac{\Delta T \cdot s + 1}{1} \qquad \text{Equation (2)}$$

$$u = \frac{\Delta T \cdot s + 1}{1} \theta_{ref} \qquad \text{Equation (3)}$$

In Equation (3), the symbol u denotes the compensation value.

According to the second embodiment, the delay time until the distal portion 34 of the treatment tool 21 starts the turn-back after the turn-back command is issued is referred to by the parameter table 57 and the compensation value of the delay time is updated. Accordingly, even when the characteristics of the wire 38 vary, it is possible to perform calibration.

Third Embodiment

A third embodiment of the present invention will be described below.

Figure 11:
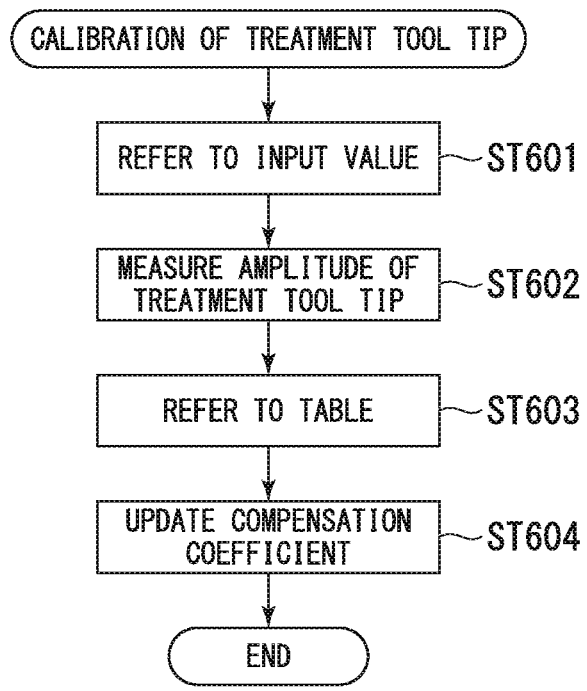
FIG. 11 is a flowchart showing calibration in a medical system according to a third embodiment.

FIG. 11 is a flowchart showing calibration in a medical system according to a third embodiment. This embodiment is different from the above-mentioned embodiments in the calibration order in the control unit 50. As shown in FIG. 11, in the calibration according to this embodiment, the compensation value is changed based on a ratio of the amplitude of displacement of the distal portion 34 of the treatment tool in response to a command and the amplitude of actual displacement of the distal portion 34 of the treatment tool 21.

In this embodiment, first, an input value is referred to (REFER TO INPUT VALUE, step ST601).

Then, the amplitude of the distal portion 34 of the treatment tool 21 is measured (MEASURE AMPLITUDE OF TREATMENT TOOL TIP, step ST602).

Subsequently, the measured amplitude is referred to by the parameter table 57 (REFER TO TABLE, step ST603) and a compensation coefficient is updated (UPDATE COMPENSATION COEFFICIENT, step ST604). The compensation value based on the compensation coefficient is expressed as u in Equation (4).

$$u = \alpha \cdot \theta_{ref} \qquad \text{Equation (4)}$$

In Equation (4), the symbol α denotes the compensation coefficient and is expressed by Equation (5). $\theta_{ref}$ is an angle command value which is included in a displacement command for the distal portion 34, and the symbol $\theta_{ref}$ denotes a response value of the angle of the distal portion 34 to the command. For example, when the actual amplitude of the distal portion 34 relative to the amplitude based on the command is ½, the compensation coefficient α is 2 and the compensation value u is $2\theta_{ref}$ based on Equation (4).

$$\alpha = \frac{\theta_{ref}}{\theta_{out}} \qquad \text{Equation (5)}$$

According to the third embodiment, by changing the compensation value based on the amplitude ratio of the angle response of the distal portion 34 of the treatment tool 21 to the command, it is possible to perform calibration even when the characteristics of the wire 38 vary.

Fourth Embodiment

A fourth embodiment of the present invention will be described below.

Figure 12:
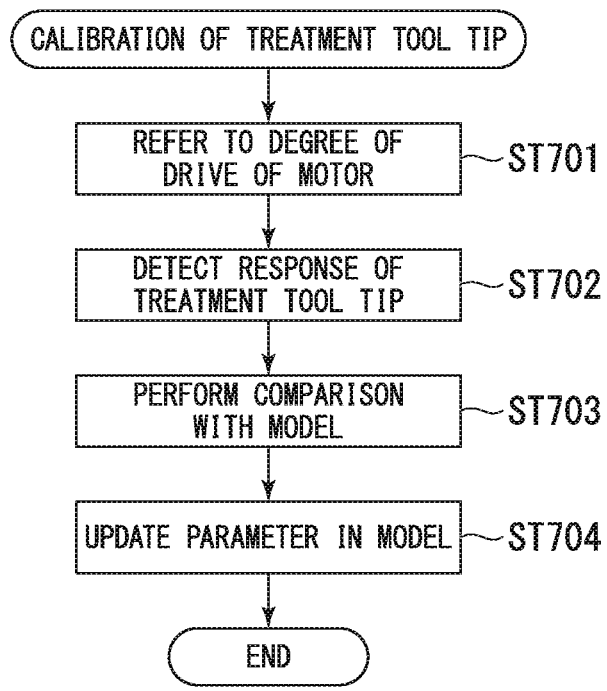
FIG. 12 is a flowchart showing calibration in a medical system according to a fourth embodiment.

FIG. 12 is a flowchart showing calibration in a medical system according to a fourth embodiment. This embodiment is different from the above-mentioned embodiments in the calibration order in the control unit 50.

As shown in FIG. 12, in the calibration according to this embodiment, a model having elasticity is supposed from an input and an angle response and the parameter table 57 is changed using the model. Here, the distal portion 34 has elasticity characteristics due to an elastic restoring force accumulated in the flexible portion 33 or an elastic repulsive force of the wire 38. Accordingly, the amplitude decreases due to the elasticity characteristics of the flexible portion 33 and the wire 38. That is, first, the degree of drive of the motor 35 acquired by the encoder 36 is referred to (REFER TO DEGREE OF DRIVE OF MOTOR, step ST701).

Then, the response of the distal portion 34 of the treatment tool 21 is detected (DETECT RESPONSE OF TREATMENT TOOL TIP, step ST702).

Subsequently, comparison with a model which is prepared in advance is performed (PERFORM COMPARISON WITH MODEL, step ST703). Here, the model is expressed by Equation (6) and Equation (7). In Equations (6) and (7), the symbol θ denotes the angle of the distal portion 34, the symbol $\theta_m$ denotes the angle of the motor 35, the symbol θ' denotes the angular velocity of the distal portion 34, the symbol J denotes the moment of inertia of the distal portion 34, the symbol $J_m$ denotes the moment of inertia of the motor 35, the symbol F denotes the torque generated from the motor 35, the symbol $k_e$ denotes the environmental stiffness in the rotating direction of the distal portion 34, the symbol c denotes the viscous frictional coefficient in the rotating direction, the symbol $f_d$ denotes the frictional torque applied to the distal portion 34, and the symbol k denotes the rigidity of the wire 38 which is converted into the rotating direction.

The detected quantity of the distal portion 34 may be a position. In this case, in Equations (6) and (7), the symbol θ denotes the position of the distal portion 34, the symbol $\theta_m$ denotes the position of the motor 35, the symbol θ' denotes the velocity of the distal portion 34, the symbol J denotes the mass of the distal portion 34, the symbol $J_m$ denotes the mass of the motor 35, F denotes the force generated from the motor 35, the symbol $k_e$ denotes the environmental stiffness in the translating direction of the distal portion 34, the symbol c denotes the viscous frictional coefficient in the translating direction, the symbol $f_d$ denotes the frictional force applied to the distal portion 34, and the symbol k denotes the rigidity of the wire 38.

$$J_m \ddot{\theta}_m = -k(\theta_m - \theta) + F \qquad \text{Equation (6)}$$

Here, the symbol em denotes a second differential of $\theta_m$.

$$J_m \ddot{\theta}_m = -k(\theta_m - \theta) + F \qquad \text{Equation (7)}$$

Here, the symbol $\ddot{\theta}$ is a second differential of θ, and the symbol $\dot{\theta}$ is equal to θ' and denotes a first differential of θ

Then, a parameter in the model is updated (UPDATE PARAMETER IN MODEL, step ST704).

The parameter in the model can be acquired by repeating calculation such that the tip angle information acquired from the image information matches the model output.

The compensation value u can be calculated by using the parameter in the model in Equations (8) and (9).

$$\Delta\theta = \frac{f_d}{k} \qquad \text{Equation (8)}$$

$$u = \Delta\theta \cdot \text{sgn}(\dot{\theta}_{ref}) \qquad \text{Equation (9)}$$

In Equation (8), the symbol $f_d$ denotes the frictional torque applied to the distal portion 34 and the symbol k denotes the rigidity of the wire 38 which is converted into the rotating direction.

In this case, it is possible to determine the compensation value by matching the command output with the model output.

According to the fourth embodiment, by changing the parameter table 57 using the model which is supposed from the input and the angle response, it is possible to perform calibration even when the characteristics of the wire 38 vary.

The model expressed by Equations (6) and (7) is an example and the model may be defined using another function.

Fifth Embodiment

A fifth embodiment of the present invention will be described below

Figure 13:
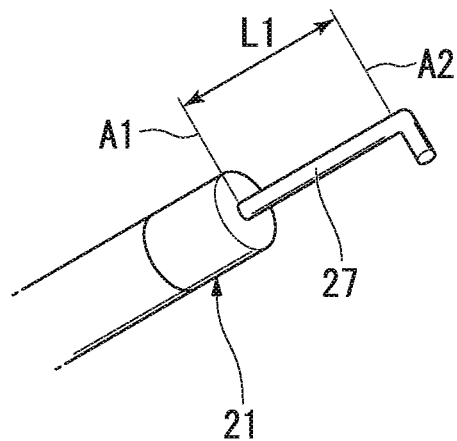
FIG. 13 is a perspective view of a distal portion when calibration is performed in a medical system according to a fifth embodiment.

FIG. 13 is a perspective view of a distal portion when calibration is performed in a medical system according to the fifth embodiment. This embodiment is different from the above-mentioned embodiments in that calibration of a degree of advance and retraction of the distal portion 34 in the axial direction of the treatment tool channel 29 is performed by the control unit 50.

As shown in FIG. 13, the treatment portion 27 is moved to advance and retract by a stroke length L1 between a position A1 and a position A2 by the treatment tool driving unit 32.

Figure 14:
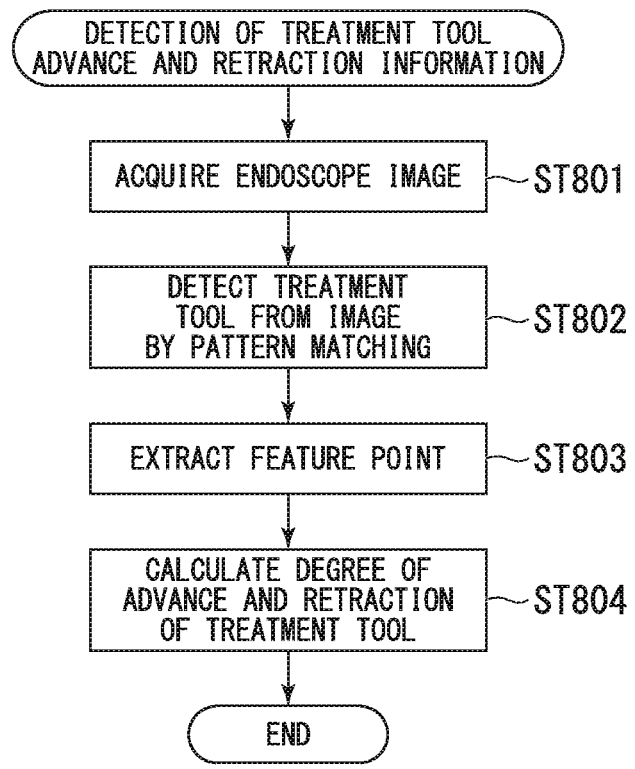
FIG. 14 is a flowchart showing an example in which calibration is performed in the medical system according to the fifth embodiment.

FIG. 14 is a flowchart showing an example in which calibration is performed in the medical system according to the fifth embodiment. As shown in FIG. 14, first, image information 59 of the endoscope device 3 is acquired (ACQUIRE ENDOSCOPE IMAGE, step ST801).

Then, the treatment tool 21 is detected from the image information 59 of the endoscope device 3 by the pattern matching (DETECT TREATMENT TOOL FROM IMAGE BY PATTERN MATCHING step ST802).

Subsequently, an identification portion (feature point) X is extracted from the detected treatment tool 21 (EXTRACT FEATURE POINT, step ST803).

Then, the degree of advance and retraction of the treatment tool 21 is calculated using the extracted identification portion X (CALCULATE DEGREE OF ADVANCE AND RETRACTION OF TREATMENT TOOL, step ST804).

Figure 15:
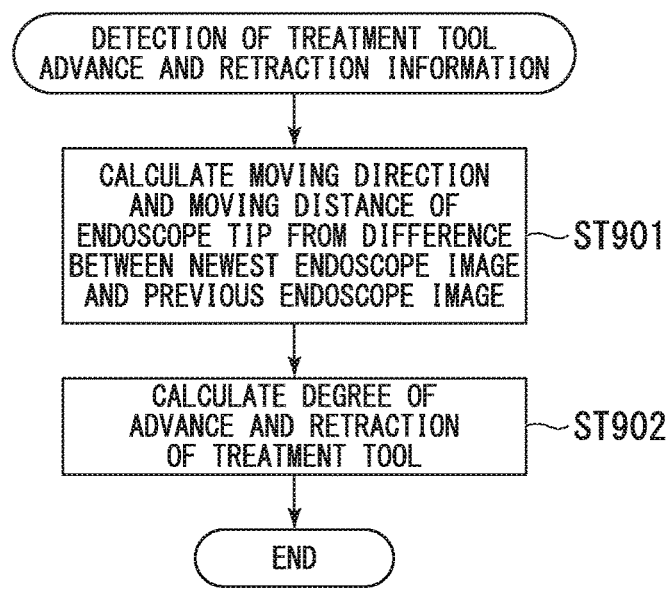
FIG. 15 is a flowchart showing another example in which calibration is performed in the medical system according to the fifth embodiment.

FIG. 15 is a flowchart showing another example in which calibration is performed in the medical system according to the fifth embodiment.

The calibration according to this embodiment may be performed using the optical flow described in the first embodiment. That is, as shown in FIG. 15, first, newest image information 59 of the endoscope device 3 is acquired. Then, previous image information 59 of the endoscope device 3 is acquired and a difference between the pieces of image information 59 is calculated, whereby a moving direction and a moving distance of the endoscope tip are calculated (CALCULATE MOVING DIRECTION AND MOVING DISTANCE OF ENDOSCOPE TIP FROM DIFFERENCE BETWEEN NEWEST ENDOSCOPE IMAGE AND PREVIOUS ENDOSCOPE IMAGE, step ST901).

Then, the degree of advance and retraction of the distal portion 34 of the treatment tool 21 is calculated (CALCULATE DEGREE OF ADVANCE AND RETRACTION OF TREATMENT TOOL, step ST902).

According to the fifth embodiment, by performing calibration using the degree of advance and retraction of the treatment portion 27 in the image information 59 of the endoscope device 3, it is possible to perform calibration even when the characteristics of the wire 38 vary.

Sixth Embodiment

A sixth embodiment of the present invention will be described below.

Figure 16:
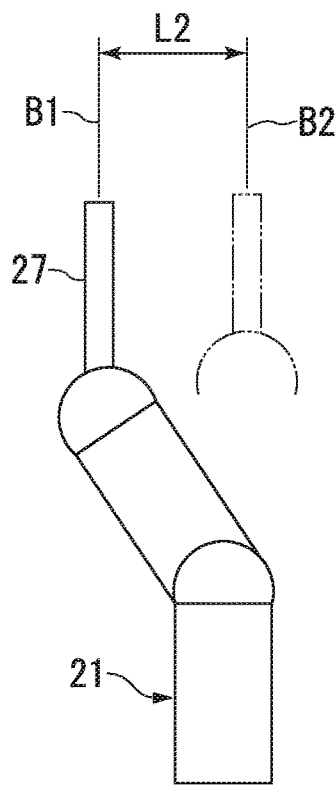
FIG. 16 is a perspective view of a distal portion when calibration is performed in a medical system according to a sixth embodiment.

FIG. 16 is a perspective view of a distal portion when calibration is performed in a medical system according to the sixth embodiment. This embodiment is different from the above-mentioned embodiments in that calibration of a degree of parallel movement of the distal portion 34 in the direction perpendicular to the axis of the treatment tool channel 29 is performed by the control unit 50.

As shown in FIG. 16, in this case, the calibration is performed using the degree of parallel movement of the treatment portion 27 in the image information 59 of the endoscope device 3 instead of the joint portion 22. The treatment portion 27 is moved in a parallel style by a stroke length L2 between a position B1 and a position B2 by the treatment tool driving unit 32.

Figure 17:
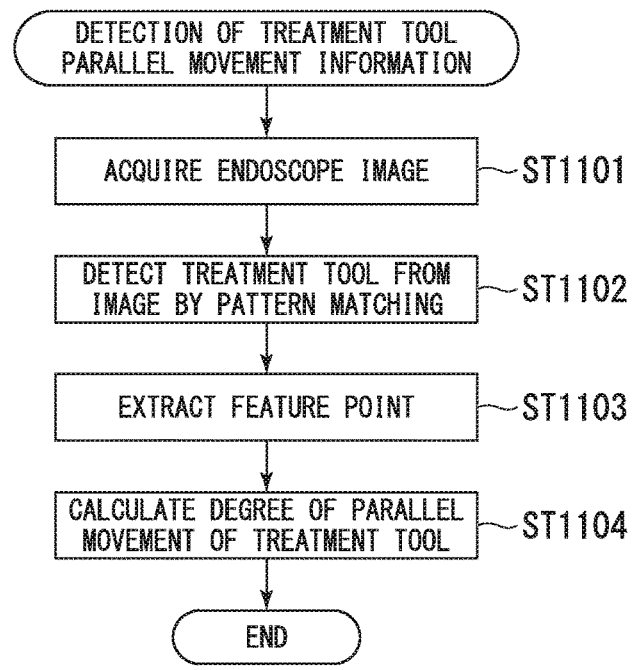
FIG. 17 is a flowchart showing an example in which calibration is performed in the medical system according to the sixth embodiment.

FIG. 17 is a flowchart showing an example in which calibration is performed in the medical system according to the sixth embodiment. As shown in FIG. 17, first, image information 59 of the endoscope device 3 is acquired (ACQUIRE ENDOSCOPE IMAGE, step ST1101).

Then, the treatment tool 21 is detected from the image information 59 of the endoscope device 3 by the pattern matching (DETECT TREATMENT TOOL FROM IMAGE BY PATTERN MATCHING step ST1102).

Subsequently, an identification portion (feature point) X is extracted from the detected treatment tool 21 (EXTRACT FEATURE POINT, step ST1103).

Then, the degree of parallel movement of the treatment tool 21 is calculated using the extracted identification portion X (CALCULATE DEGREE OF PARALLEL MOVEMENT TOOL, step ST104).

Figure 18:
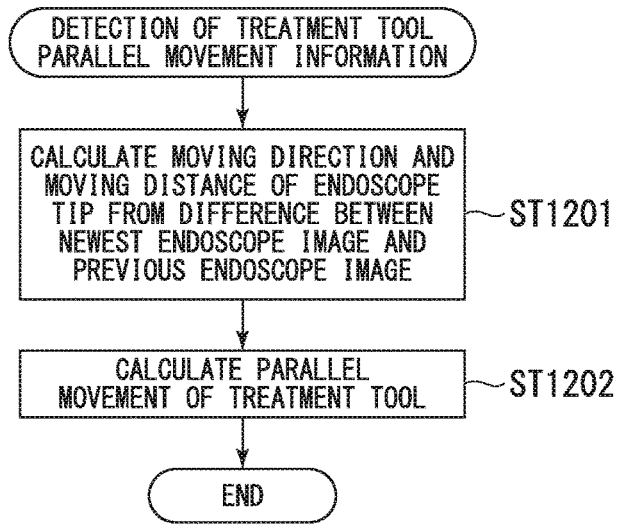
FIG. 18 is a flowchart showing another example in which calibration is performed in the medical system according to the sixth embodiment.

FIG. 18 is a flowchart showing another example in which calibration is performed in the medical system according to the sixth embodiment. The calibration according to this embodiment may be performed using the optical flow which is described in the first embodiment. That is, as shown in FIG. 18, first, newest image information 59 of the endoscope device 3 is acquired. Then, previous image information 59 of the endoscope device 3 is acquired and a difference between the pieces of image information 59 is calculated, whereby a moving direction and a moving distance of the endoscope tip are calculated (CALCULATE MOVING DIRECTION AND MOVING DISTANCE OF ENDO-SCOPE TIP FROM DIFFERENCE BETWEEN NEWEST ENDOSCOPE IMAGE AND PREVIOUS ENDOSCOPE IMAGE, step ST1201).

Then, the degree of parallel movement of the distal portion 34 of the treatment tool 21 is calculated (CALCULATE DEGREE OF PARALLEL MOVEMENT OF TREATMENT TOOL, step ST1202).

According to the sixth embodiment, by performing calibration using the degree of parallel movement of the treatment portion 27 in the image information 59 of the endoscope device 3, it is possible to perform calibration even when the characteristics of the wire 38 vary.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A medical system comprising:
   a treatment tool comprising:
      a treatment portion configured to perform treatment on a living body;
      a joint configured to change a direction of the treatment portion;
      a flexible tube connected to the joint; and
      an actuator connected to the flexible tube, the actuator being configured to activate the joint;
   an endoscope comprising an imaging unit configured to acquire at least an image including at least the joint in an imaging field of view; and
   a controller configured to control an operation of the treatment tool based on the image;
   wherein the controller is further configured to:
      acquire a parameter from a table for activating the joint;
      generate a command for activating the actuator according to the acquired parameter;
      activate the joint by activating the actuator based on the command;
      calculate at least one of a position and an orientation of the joint according to the image acquired by the imaging unit;
      subsequent to the calculating of at least one of the position and the orientation of the joint, deactivate the actuator;
      calculate displacement of the joint according to at least one of the position and the orientation of the joint;
      calculate a compensation value according to the displacement and the command; update the parameter based on the compensation value; and
      rewrite the updated parameter in the table.

2. The medical system according to claim 1, wherein the controller is further configured to calculate a joint angle of the joint by pattern matching using the image.

3. The medical system according to claim 1, wherein the controller is further configured to calculate the displacement of the joint in the image, the displacement being calculated from a difference between a newest image and an image acquired immediately before the newest image in time series.

4. The medical system according to claim 1, wherein the controller is configured to displace the joint until the joint appears in the image, in a case when the joint cannot be specified in the image.

5. The medical system according to claim 1, further comprising a display configured to display the image;
   wherein the controller is further configured to:
      determine that the joint is located outside the imaging field of view of the imaging unit in a case where the joint cannot be specified in the image, and
      output an instruction image instead of the image to the display, the instruction image being generated by superimposing a specifiable area for the joint on the image;
      display the instruction image on the display when the instruction image is received instead of the image; and
      calculate at least one of the position and the orientation of the joint using an image in which the joint is located in the specifiable area.

6. The medical system according to claim 1, wherein the treatment tool includes an identification portion for identifying a configuration of the treatment tool in at least one of the treatment portion and the joint; and
   the controller is configured to specify the treatment tool based on the identification portion.

7. The medical system according to claim 1, wherein the controller is configured to:
   calculate a hysteresis width based on a degree of drive of the actuator until the displacement of the joint is started after the command is issued; and
   set the calculated hysteresis width as the compensation value.

8. The medical system according to claim 6, wherein the controller is configured to change the parameter so as to correspond to the treatment tool which is specified based on the identification portion.

* * * * *